(12) United States Patent
Thomke et al.

(10) Patent No.: US 7,618,417 B2
(45) Date of Patent: Nov. 17, 2009

(54) CLAMP FOR MULTIPLE ROD SHAPED ELEMENTS

(75) Inventors: Roland Thomke, Bellach (CH);
Vinzenz Burgherr, Bern (CH);
Christian Lutz, Solothurn (CH);
Damian Fankhauser, Bern (CH);
Clemens Dransfeld, Niederlenz (CH);
René Fischer, Zurich (CH)

(73) Assignee: Stryker Trauma S.A. (CH)

( * ) Notice: Subject to any disclaimer, the term of this patent is extended or adjusted under 35 U.S.C. 154(b) by 648 days.

(21) Appl. No.: 11/108,492

(22) Filed: Apr. 18, 2005

(65) Prior Publication Data

US 2006/0052781 A1 Mar. 9, 2006

(30) Foreign Application Priority Data

Aug. 20, 2004 (EP) .................. 04405522

(51) Int. Cl.
*A61F 5/04* (2006.01)
(52) U.S. Cl. .................. 606/59; 606/324; 606/54; 403/329
(58) Field of Classification Search .................. 606/59, 606/53, 57, 54, 55, 56, 58; 403/385, 397, 403/329, 781, 782, 783, 776, 761, 803
See application file for complete search history.

(56) References Cited

U.S. PATENT DOCUMENTS

| | | | | |
|---|---|---|---|---|
| 1,729,613 A | * | 10/1929 | Gross | 439/761 |
| 4,135,505 A | * | 1/1979 | Day | 606/59 |
| 4,169,652 A | * | 10/1979 | Hockele et al. | 439/781 |
| 4,293,176 A | | 10/1981 | Lindlöf | |
| 4,469,367 A | * | 9/1984 | Kuttler et al. | 296/97.9 |
| 4,496,263 A | * | 1/1985 | Laarhoven | 403/402 |
| 5,160,335 A | | 11/1992 | Wagenknecht | |
| 5,376,090 A | * | 12/1994 | Pennig | 606/54 |
| 5,728,096 A | | 3/1998 | Faccioli et al. | |
| 5,752,954 A | | 5/1998 | Mata et al. | |
| 5,891,144 A | | 4/1999 | Mata et al. | |
| 6,342,054 B1 | * | 1/2002 | Mata | 606/59 |
| 6,423,061 B1 | * | 7/2002 | Bryant | 606/57 |
| 6,565,564 B2 | | 5/2003 | Hoffman et al. | |
| 2002/0142674 A1 | * | 10/2002 | Chadbourne et al. | 439/783 |
| 2003/0191467 A1 | * | 10/2003 | Hoffmann-Clair et al. | 606/59 |
| 2006/0167453 A1 | * | 7/2006 | Hoffmann-Clair et al. | 606/59 |

FOREIGN PATENT DOCUMENTS

| | | |
|---|---|---|
| DE | 197 53 010 | 6/1999 |
| EP | 0 700 664 A | 3/1996 |
| WO | WO-97/35527 | 10/1997 |

OTHER PUBLICATIONS

KZ V Kurganskogo Nauchnogo Tse; Abbildungen 1-3; Feb. 15, 1991 SU 1 627 161 A.
European Search Report dated Jan. 18, 2005.

* cited by examiner

*Primary Examiner*—Eduardo C Robert
*Assistant Examiner*—Jan Christopher Merene
(74) *Attorney, Agent, or Firm*—Lerner, David, Littenberg, Krumholz & Mentlik, LLP

(57) ABSTRACT

A clamping element for the clamping of multiple rod-shaped elements has two opposing jaws, which have a number of corresponding grooves for the acceptance of a corresponding number of rod-shaped elements such as bone pins. Spring elements are provided, with which in the resting position the closed jaws are tensed, to hold the rod-shaped elements in position.

14 Claims, 9 Drawing Sheets

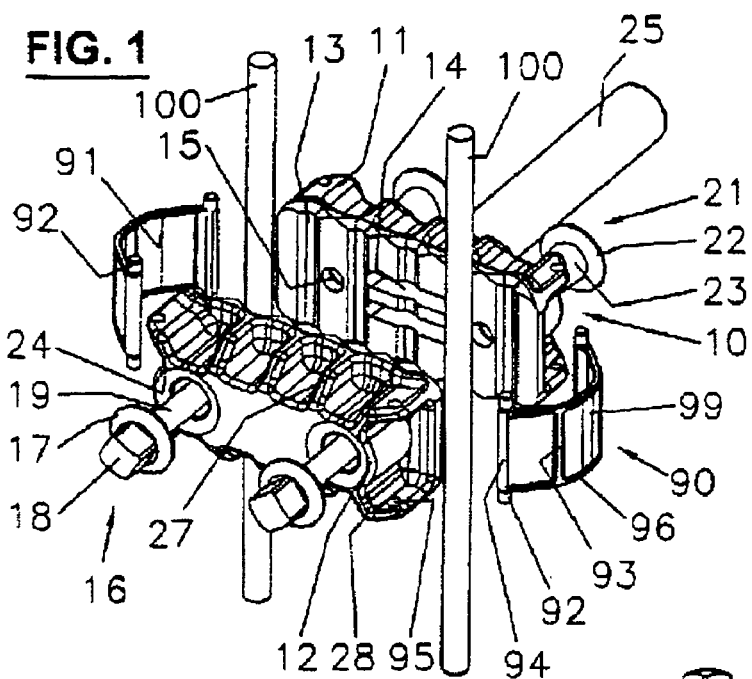
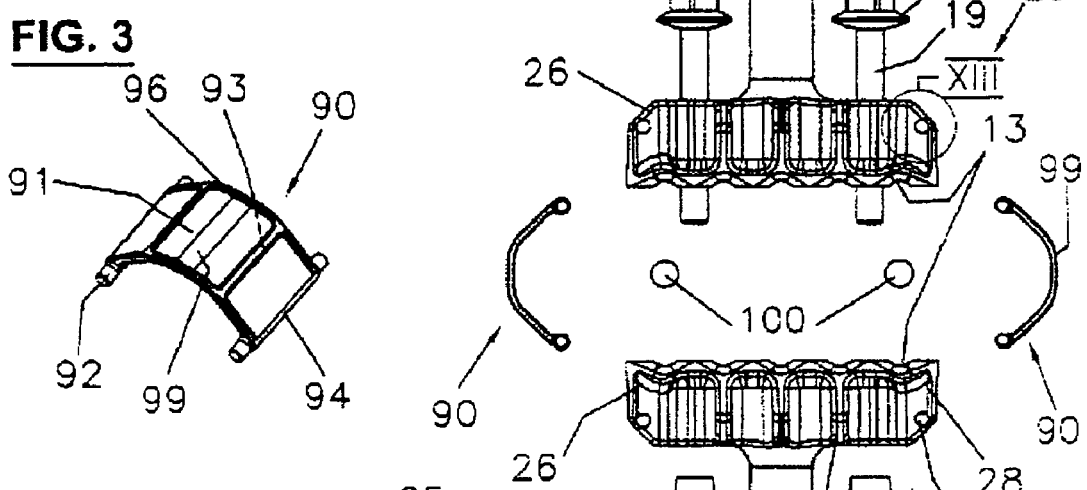
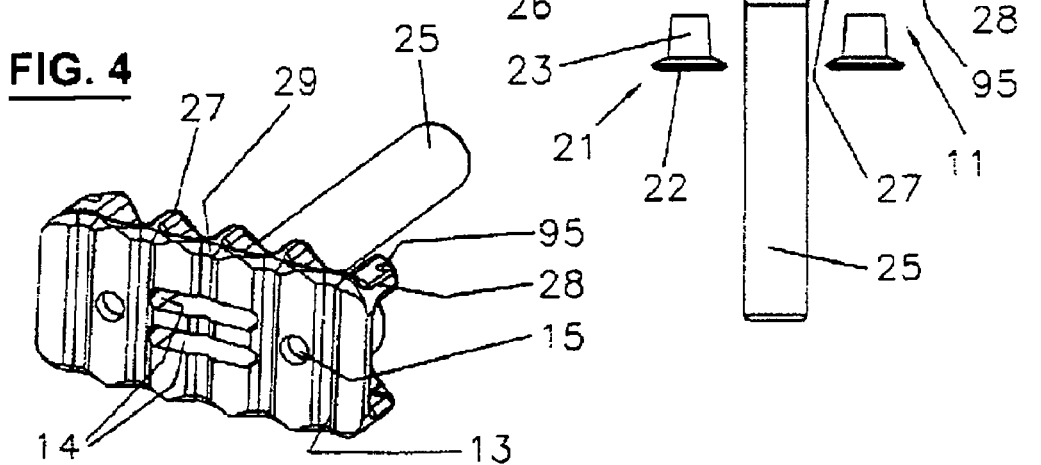

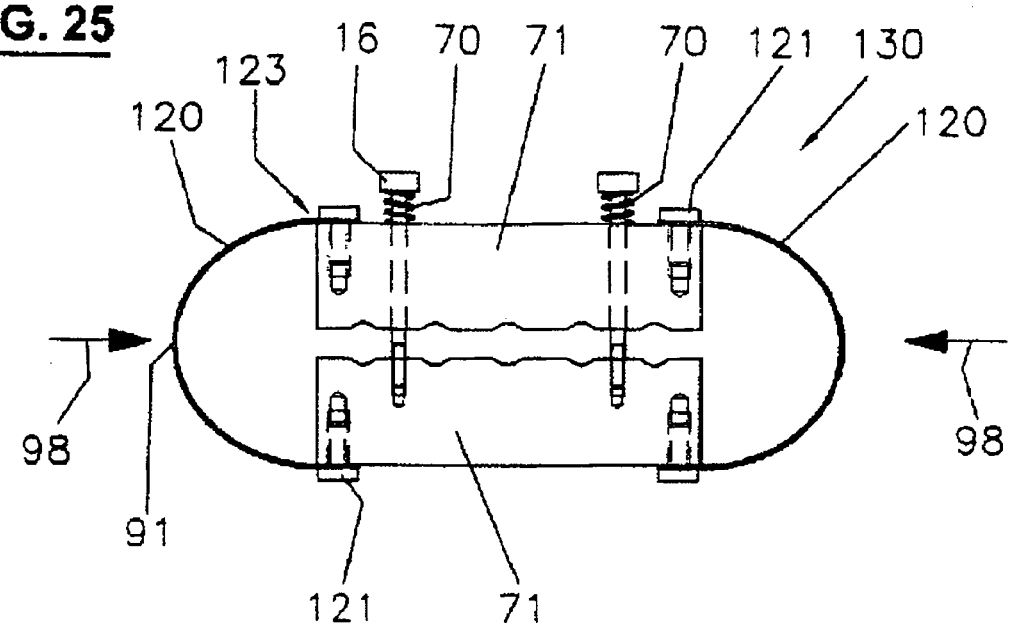
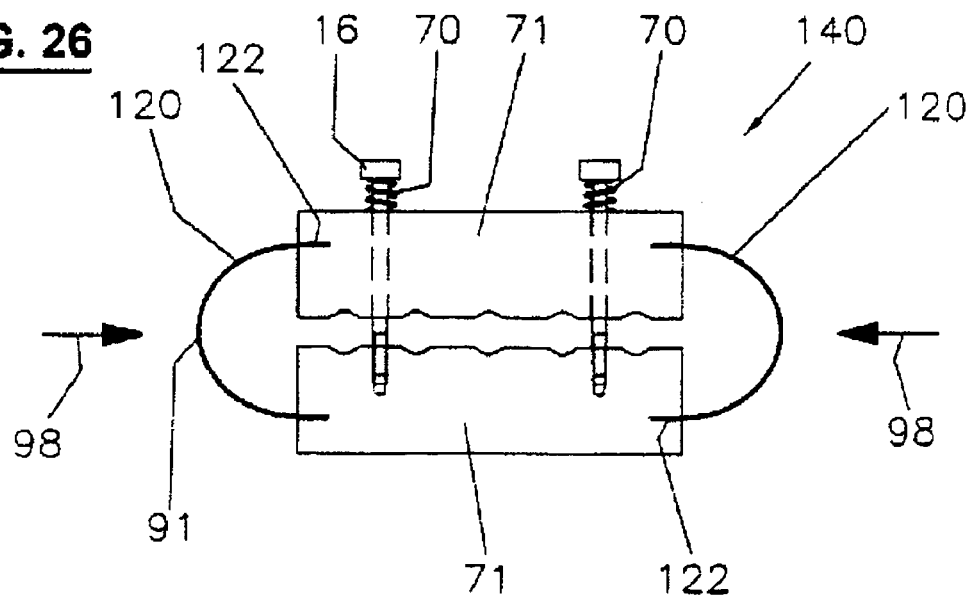

CLAMP FOR MULTIPLE ROD SHAPED ELEMENTS

BACKGROUND OF THE INVENTION

The invention concerns a clamping element for the clamping of multiple rod-shaped elements, for example pins, and particularly a clamping element for the stabilization of bone fragments.

PRIOR ART

U.S. Pat. No. 6,565,564 describes such a clamping element for the clamping of multiple pins that has, on two opposing jaws, a number of parallel grooves for the acceptance of a corresponding number of rod-shaped elements. Two bores at right angles to the grooves are provided in the jaws, through each of which a connecting screw can be inserted.

Such a clamping element has the advantage that several pins arranged next to each other can form a defined structure over the broken pieces, by means of which the connecting screws coming out of a jaw can be screwed into one of the interior-threaded nuts inserted in the other jaw, in order to close the jaws.

A disadvantage of the known device is that the clamping element may be closed only slowly through the tightening of various screws.

Spiral springs are inserted between the jaws and around both connecting screws, in order to push the jaws at rest away from each other and to be able to more easily insert the clamping element onto the pins.

Starting from this prior art, one aspect of the current invention to propose a simple clamping element that allows a faster fixing of inserted pins.

An additional aspect of the invention is to create a cost-effective one-way clamping element, especially one made of injection-molded plastic.

SUMMARY OF THE INVENTION

The two jaws are connected by means of two spring elements to a preferably one-piece clamping jaw, whereby through simple activation of the spring elements the clamping jaws may be somewhat separated from each other, the pins positioned and finally blocked. This enables such a clamping element to be manipulated in a simpler fashion.

The invention relates to a clamp for bone pins which has a first jaw member with a bone pin engaging surface including a plurality of elements, such as grooves, for locating a plurality of bone pins. The first jaw member has external surfaces which may include elements for engaging an external fracture fixation system. A second jaw member is provided having a bone pin contacting surface. A pair of clamping elements extends through the second jaw members for moving the bone pin engaging surfaces towards one another to clamp the bone pins therebetween. A pair of spring elements each engaging an external surface of the first jaw member act to bias the first and second jaw members towards one another. In the preferred embodiment, each of the pair of spring elements engage external surfaces of both the first and second jaw members. Preferably the clamping elements are threaded elements such as threaded rods extending through bores in both the first and second jaw members. The spring elements may be coil springs surrounding each of the threaded elements acting on an external surface of at least one of the first and second jaw members.

Additional advantageous sample embodiments are set forth in the subordinate claims.

BRIEF DESCRIPTION OF FIGURES

The invention will now be described in greater detail, using the illustrative examples.

The invention will be understood more fully, while still further objects and advantages will become apparent, in the following detailed description of the preferred embodiments of the invention illustrated in the accompanying drawing, in which:

FIG. 1 is a perspective exploded view of a first sample embodiment of a jaw pursuant to the invention;

FIG. 2 is a top view of a second sample embodiment of a clamping element similar to FIG. 1;

FIG. 3 is a perspective view of a spring element of the clamping element according to FIG. 1 or 2;

FIG. 4 is a perspective view of a jaw of the clamping element according to FIG. 1 or 2;

FIG. 25 is a schematic side view of a sixth sample embodiment of a clamping element according to the invention, without pins; and FIG. 26 is a schematic side view of a seventh sample embodiment of a clamping element pursuant to the invention, without pins.

DETAILED DESCRIPTION OF THE PREFERRED SAMPLE EMBODIMENTS

Figure 5:
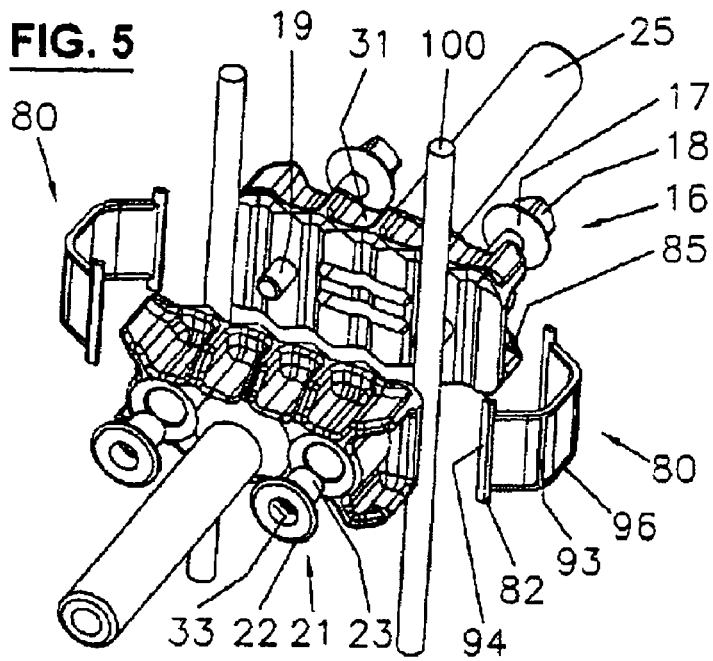
FIG. 5 is a perspective view of a third sample embodiment of a clamping element pursuant to the invention.

FIG. 1 shows a perspective exploded view of a preferred embodiment of a clamping element 10 pursuant to the invention. The clamping element 10 consists of two jaws 11 and 12. These jaws 11 and 12 are essentially similarly shaped on the sides facing each other. Only on the side turned away is jaw 11 provided with a correspondingly-shaped rod 25, while jaw 12 exhibits a connection leading outward.

The jaws 11 and 12 are here provided with five parallel grooves 13. More or fewer grooves 13 may also be provided. Different grooves 13 may also run at an angle to each other, for example at a 30-degree angle. The grooves 13 may also be arranged partly parallel to one another and partly in various angles to one another.

The jaw 11 is provided, on the inner side opposite the rod 25, with two slots 14 with almost parallel side walls that run perpendicular to the grooves 13, and that end in a jaw itself. On the side of each of the jaws 11 and 12, two bores 15 are provided, that on the outside have a conical mounting 24. A screw 16 with a conical complementary flange 17 and a square head 18 is inserted in the bore 15 of one jaw, here 12, from one side, and from bore 15 of the other jaw, here 11, a nut 21 with a conical flange 22 and casing 23 is inserted. The threaded screw shank 19 grips the nut 21 through the bore 15 into the casing 23 and permits the movement of the jaws 11 and 12 toward each other. The bore 15 and the complementary casing 23 can, for example, also be made cylindrical.

The combination of screw 16 and nut 21 can also be replaced by a single screw to be screwed into the other jaw. Threading may be provided in the bore 15 or the screw may exhibit self-tapping threading. Quite generally, a locking element may be provided which may be a lever locking element or a bayonet lock. Among these locking elements may also be supporting disks or toothed disks, which, for the sake of simplicity, are not shown in the drawings. The two jaws to be inserted opposite each other (for example 11 and 11, or 11 and 12), may also be manufactured using the same tool, especially a multiple tool with almost identical molds, in which the bore 15 of one injection mold is designed for the direct mounting of a screw with a smaller diameter than the bore (or the threading).

Between the jaws 11 and 12 rod-shaped elements, such as pins 100, are inserted. Here two pins 100 are shown.

The jaws 11 and 12 exhibit full-type silicone in the area of the screw mounting. On the rims on the long sides only three ribs 27 are provided. On the corners of each jaw 11 or 12 are altogether four spring-mounted ribs 28. These spring-mounted ribs 28 each have a small round through hole 95 for the acceptance of a corresponding round plug 92 of a spring element 90. On one narrow side of a jaw 11 or 12 both holes 95 are aligned and lie parallel to the main axis of the grooves 13 provided here.

In this way, a spring element 90 can be inserted, as shown in FIG. 3 in its tightened position, in which a perspective view of the spring element 90 is shown, i.e. for an injection-molded part in its loosened state; both axes formed by the plugs 92 would be almost parallel to each other. The same is true for a spring element 90 which might for example be in the shape of a stamped metal part. It has one stem 94 on the free end. The stem 94 itself ends on both ends in round plugs 92, which can engage in two holes 95. Both stems 94 are connected to each other through two flexible longitudinal ribs 96 on the sides. Furthermore, two reinforcing perpendicular ribs 93 are provided. Between the grooves mentioned, spring element fields 91 are extended. The length and arc shape of the spring element 90 is shown in such a way that, when inserted in the hole 95, it moves the two jaws 11 and 12 toward each other, i.e. closes them.

It is also necessary to press on the center surfaces as the area of manipulation 99, in order to reduce the curvature of the spring element 90 on the way to the free ends, to separate the two stems 94 from each other and thereby open the associated jaws 11 and 12. In letting go of the spring element 90, the clamping element 10 then automatically closes.

FIG. 2 shows a top view of a second embodiment of a clamping element 20 similar to FIG. 1. The same features are in each case provided with the same reference numbers. The difference lies in the fact that two identical jaws 11 are used. Orea (?) XIII denotes a cutout section that is shown enlarged in FIG. 13.

FIG. 4 shows a perspective view of a jaw of the clamping element according to FIG. 1 or FIG. 2. It can be recognized that opposite each groove 13 there is a reinforcing rib 27. Furthermore, a spring-mounted reinforcing rib 28 is provided for the side grooves 13 and the mounting of the spring element 90. Each groove is equipped with milling/toothing 29 for easy insertion of the pin 100.

Figure 6:
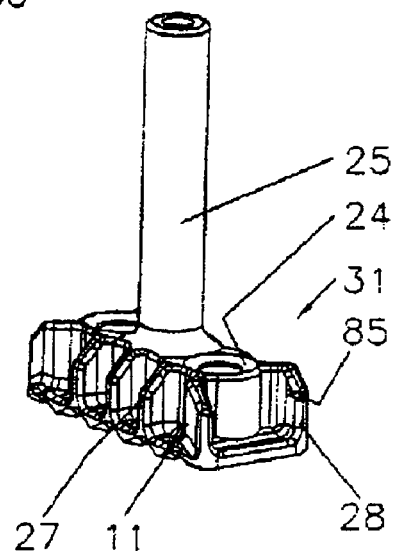
FIG. 6 is a perspective view of a jaw of the clamping element according to FIG. 5.
Figure 7:
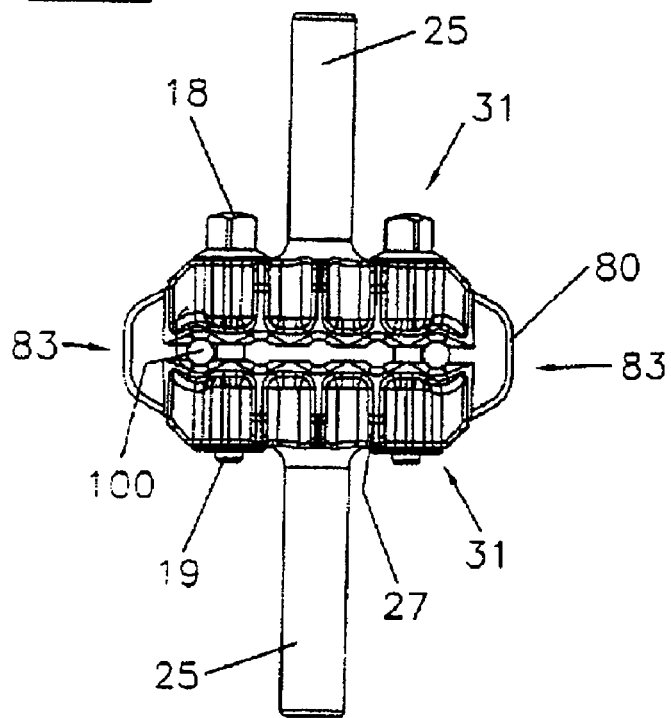
FIG. 7 is a top view of the clamping element according to FIG. 5.

FIG. 5 shows a perspective view of a third embodiment of a clamping element 30 pursuant to the invention. FIG. 6 shows a perspective view of a jaw 31 of the clamping element 30 according to FIG. 5, FIG. 7 a top view of the clamping element according to FIG. 5, and FIG. 8 a perspective view of a spring element 80 of the clamping element 30. The jaws 31 are essentially identical in form to the jaws 11. The only difference concerns the spring-mounted rib 28. This has slits 85 arranged on the interior. These slits 85 are rectangular-shaped hollows, which may of course be fabricated by injection molding as well.

The spring element 80 has a similar spring leaf 91, which is surrounded by ribs 93 and 96. The lateral stems 94 are rectangular here and end in similarly rectangular plugs 82. Through pressing on the center area of manipulation 89 of the leaf spring 91 in the direction of the arrow 83 according to FIG. 7, the two jaws 31 separate from each other and thus release the pins 100. These pins 100 can also be supplemented by others or their position may be modified, etc. It is preferable that the outwardly-raised ribs 93 and 96 help to define the area of manipulation, for example for the cupping of user's thumb and forefinger, so that he cannot slip.

Figure 9:
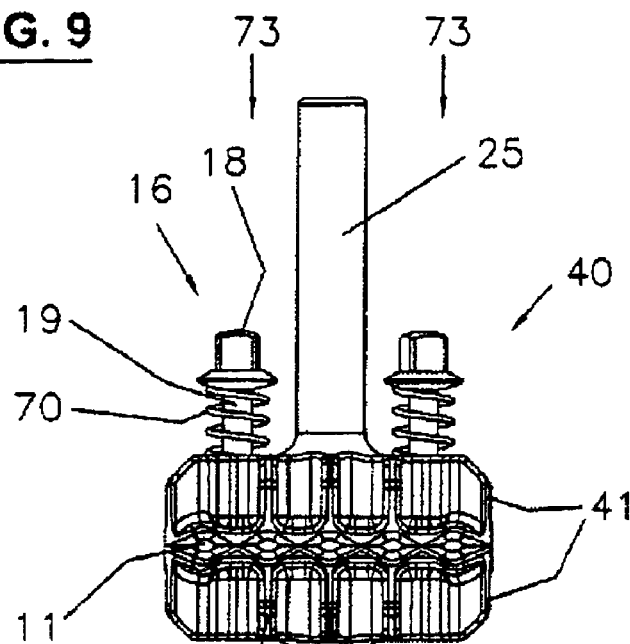
FIG. 9 is a top view of a fourth sample embodiment of a clamping element pursuant to the invention without pins.
Figure 10:
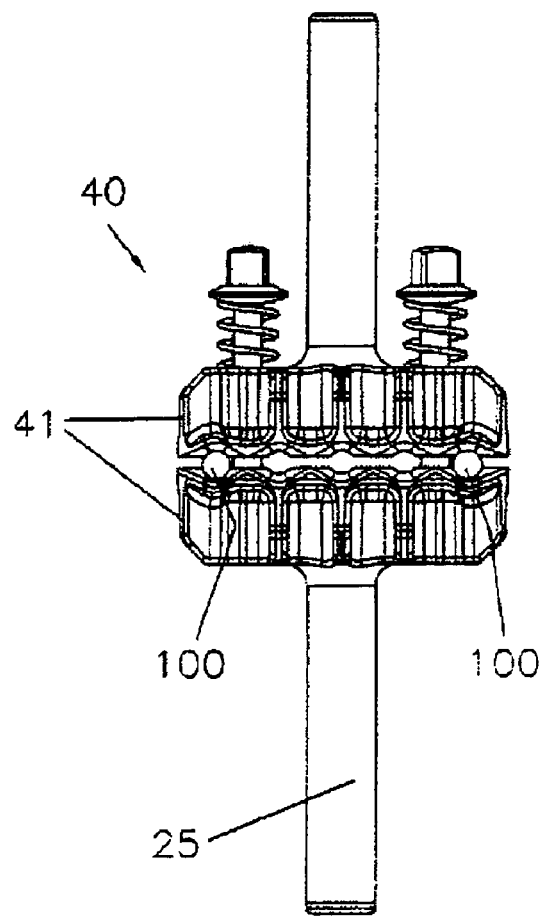
FIG. 10 is a top view according to FIG. 9 with pins inserted.

FIG. 9 shows a top view of a fourth embodiment of a clamping element 40 pursuant to the invention, without pins and FIG. 10 shows the top view according to FIG. 9 with pins 100 inserted. In the sample embodiment according to FIG. 9, spring elements 70, here spiral springs, are arranged around the two screws 16 and are supported on one side on the screw mounting 24 and on the other side on the underside of the flange 17 of the screw head 18. Thus the springs 70 press the jaws 41 together. If upper rod 25 shown in the drawing is already fixed, then by pressing in the direction of the arrow 73, for example, on both screw heads 18, the jaw 41, shown below on the drawing, may be lifted from the upper one in order to create a greater space between the grooves 14 and to be able to push in the pins 100. The spiral springs 70 are generally made of metal, but may also be made of plastic. They might also be perforated spring-washer packages or other spring elements.

Figure 11:
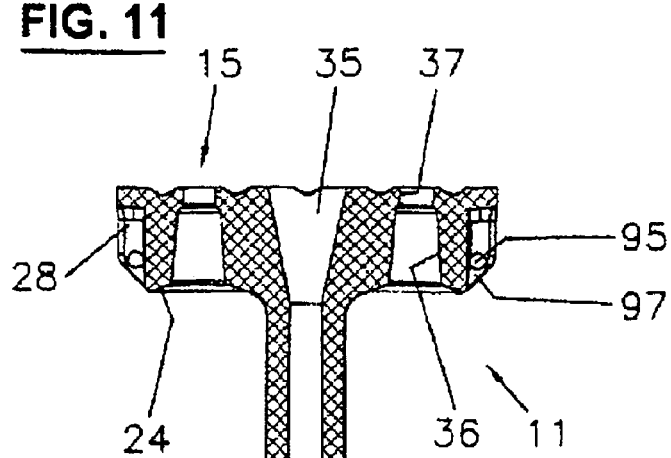
FIG. 11 is a sectional view through a jaw similar to FIG. 4.
Figure 12:
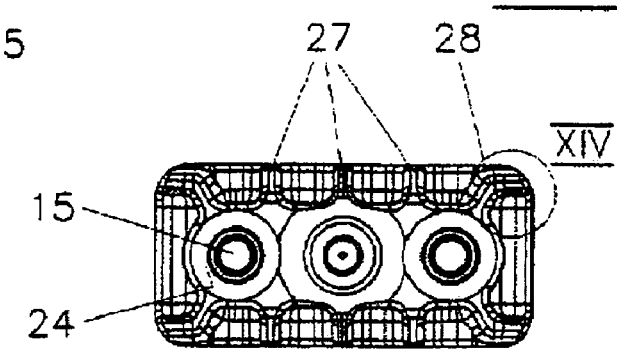
FIG. 12 is a top view of the jaw according to FIG. 11.
Figure 13:
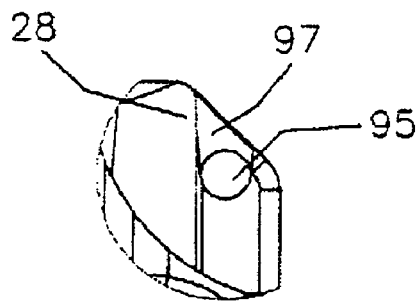
FIG. 13 is an enlarged side view of the jaw according to FIG. 11.
Figure 14:
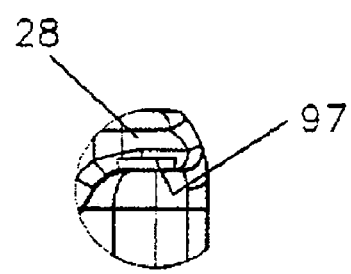
FIG. 14 is an enlarged top view of the jaw according to FIG. 11.

FIG. 11 shows a sectional view through a jaw 11 similar to FIG. 4, in which by way of overview, FIG. 12 shows a top view of the jaw 11 according to FIG. 11, FIG. 13 shows an enlarged side view of a cutout of the same jaw 11, and FIG. 14 shows an enlarged top view of the same cutout of the jaw 11 according to FIG. 11.

It may be recognized that the bore 37 in the area of the grooves 14 is a cylindrical bore with a diameter of, for example, 5 mm. It may exhibit on the interior three, four or more thin grooves of, for example, 0.5 millimeters in height, in order to guide the screw 16 centered. Connected to it is a bore space that widens conically, which may, for example increase to 8 millimeters. Finally the bore 15 opens onto a screw mounting 24 with a diameter of, for example, 14 millimeters and a rim with an exterior opening angle of 60 degrees. The bore space 36 can be equipped with a conical interior threading, in order to securely accept the casing 23 of the nut 21. It could, however, also be pressed into an interference fit.

The central bore 35 can take over the function of the slits 14, i.e. to be able to use a simpler form for injection molding technology.

On the side in the sectional view, the spring mounted rib 28 may be seen arranged behind the cutting plane, in which the way to the through hole 95 is equipped with a diminishing indentation 97, so that this indentation 97 offers a guide for the plugs 92. This is particularly visible in FIGS. 13 and 14. The indentation 97 is one-half millimeter, which is enough for a guiding function. If a suitable component technology is used, indentation 97 may also be omitted.

The grooves 14 cover an angle area of 120 degrees and exhibit a curvature radius of 2 millimeters.

Figure 8:
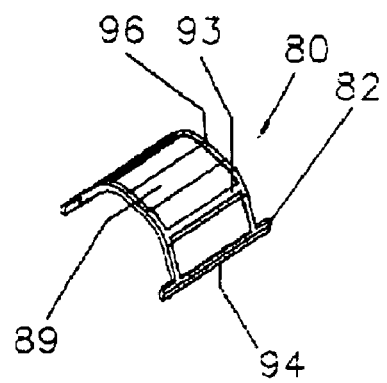
FIG. 8 is a perspective view of a spring element of the clamping element according to FIG. 5.
Figure 15:
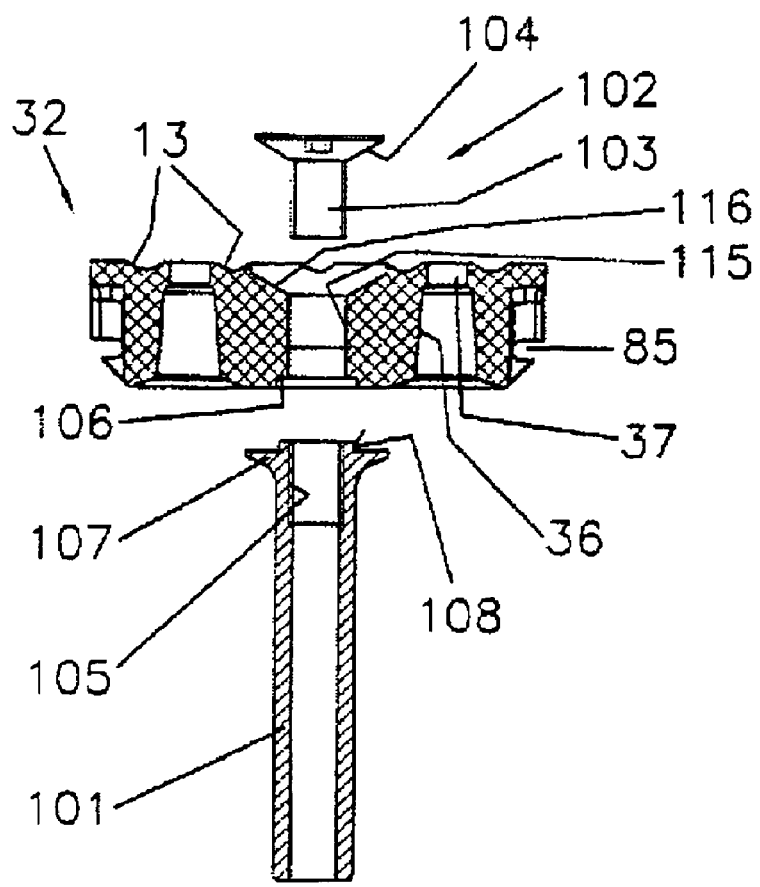
FIG. 15 is a sectional view through a jaw with attachable rod for a spring according to FIG. 8.
Figure 16:
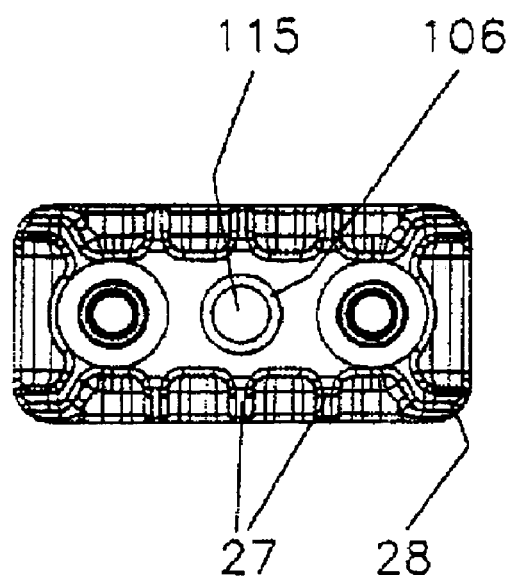
FIG. 16 is a top view of the jaw according to FIG. 15.

FIG. 15 shows a sectional view through a jaw 32 similar to FIG. 6 with attachable rod and for a spring element according to FIG. 8, and FIG. 16 shows a top view of this jaw 32. The jaw 32 has an interior bore 115 with a conical aperture 116 on the side facing the grooves 13. On the opposite side it has an indentation 106 exhibiting a larger diameter.

This enables the versatile insertion of the jaws 32 through the insertion by the operator of an attachable rod 101 in the desired length. The attachable rod 101 is hollow at least in the end area intended for mounting and has interior threading 105. It has a widening flange 107 and a narrower base 108, which may be inserted into indentation 106. Then the fastening screw 102, pushed in from the opposite side can engage with its exterior threading 103 onto the interior threading 104, such that in tightening the screw, the conically widened head 104 comes out of the aperture 116. In addition to this form of fastening using a screw 102, other locking forms such as bayonet locks or lever locks may be provided. The rod 101 to be inserted can also itself have on its end, or on both ends, instead of the flange 107, exterior threading, which screws into an interior threading provided in the bore 115 or in a casing inserted into the bore 115 from the opposite side.

What is essential and advantageous for the operator is the opportunity to start from jaw 32, and through the attachment of a rod 101 chosen by him for its desired configuration, and especially length, to fabricate a jaw that is particularly suitable for insertion, which differs from the previously configured jaw 11 or 41.

The spring mounted rib 28 has through slits 85 in which, for example, a spring element according to FIG. 8 may be inserted.

This description, however, is to be understood such that individual elements may be coupled with each other as desired, or that any spring element (metal, leaf springs, individual injection-molded parts, 2K-injection-molded parts), can be combined with any type of mounting (slit or hole, etc.) and any type of jaw (groove orientation and/or rod mounting).

Figure 17:
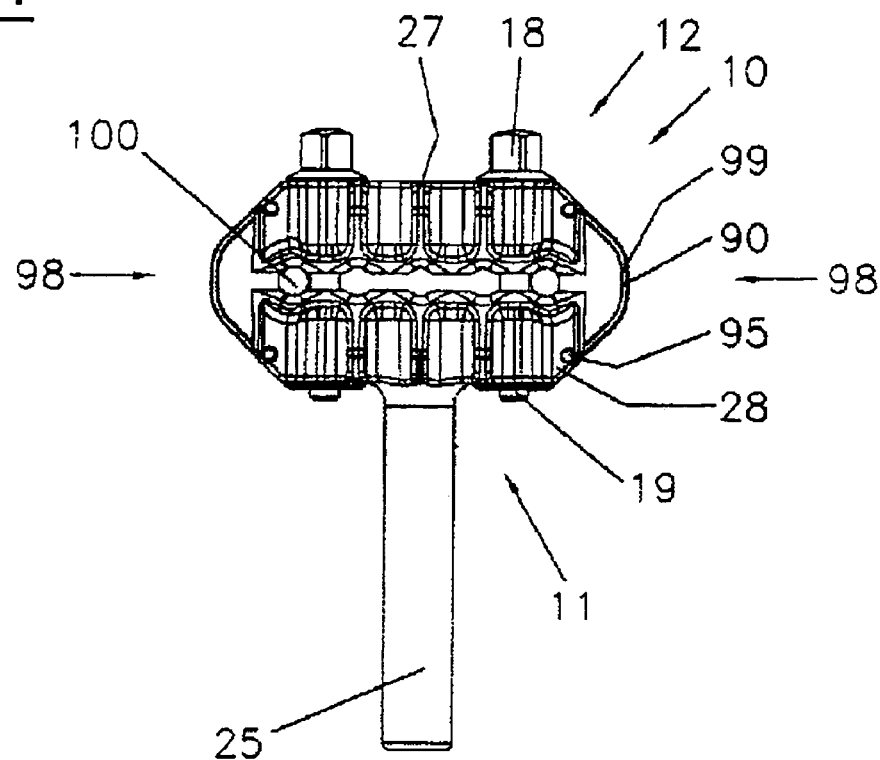
FIG. 17 is a side view of the clamping element according to FIG. 1.
Figure 18:
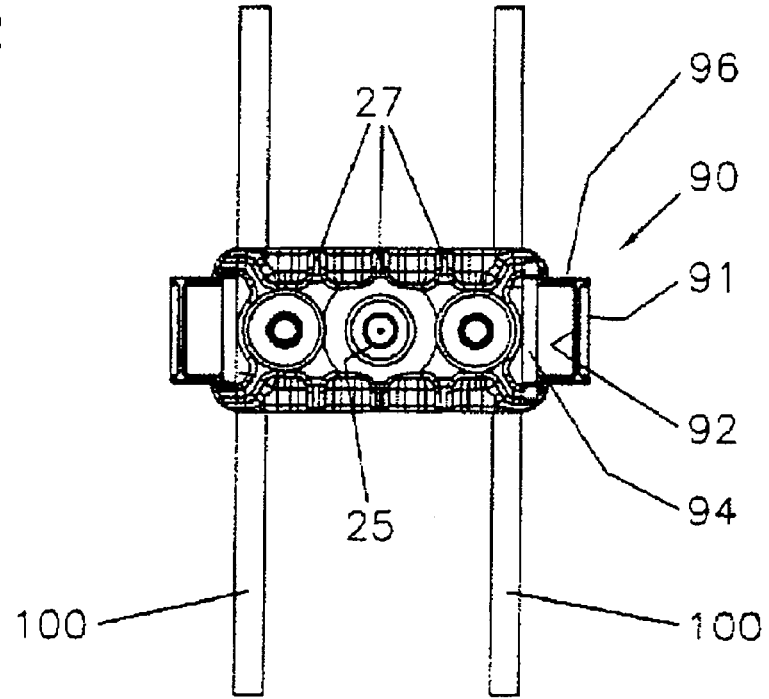
FIG. 18 is a top view of the clamping element according to FIG. 1.
Figure 22:
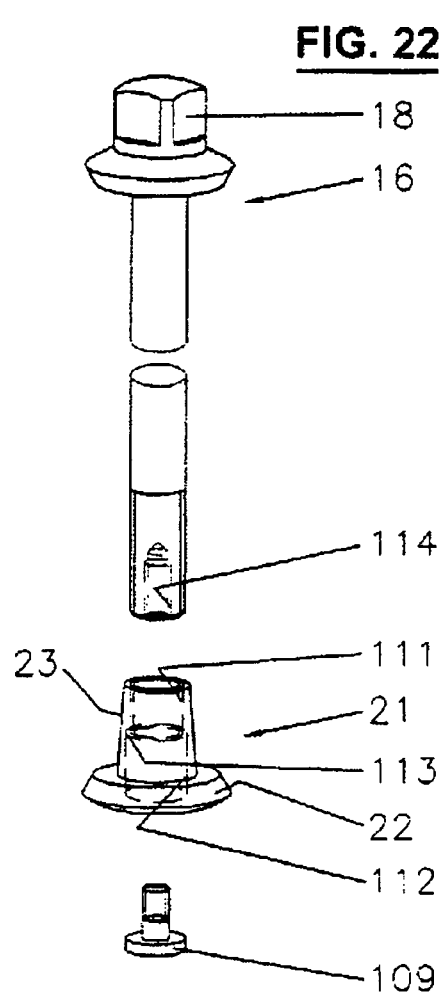
FIG. 22 is a partly sectional side view of a locking screw, a nut and a safety screw for a jaw.

FIG. 17 shows a side view of the clamping element 10 according to FIG. 1, and FIG. 18 a top view of this clamping element 10. It may be seen that the screws 16 with their screw bodies 19 pass through the nuts 21. It would also be possible for a safety screw to be inserted in an interior threading in the shank end of the screw 16, in which a shoulder in the nut 21 assures that the screws 18 and the nuts 21 are undetachably connected, as shown in FIG. 22. In other sample embodiments, the non-detachability can be assured through wobble-rivets in the screw 16.

In FIG. 17 it may be seen that by means of bilateral pressure on the spring element 90 in the direction of the arrow 98 the two jaws 11 may be further freed from each other and thus the pins 100 released.

Figure 19:
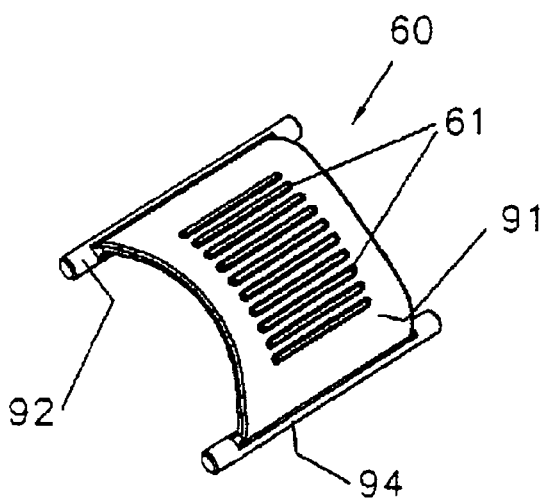
FIG. 19 is a perspective view of a spring element according to another sample embodiment for a jaw according to FIG. 4.
Figure 20:
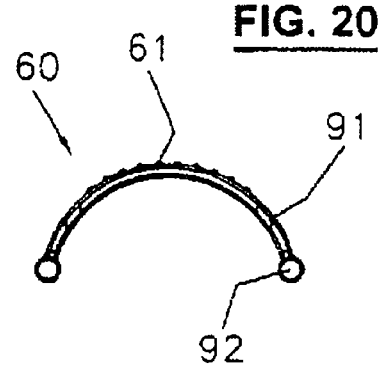
FIG. 20 is a side view of the spring element according to FIG. 19.
Figure 21:
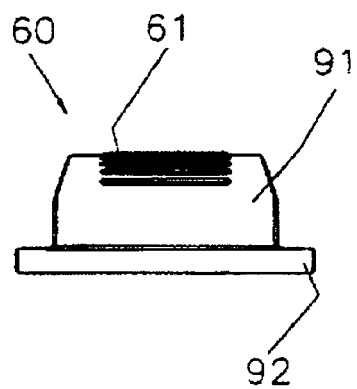
FIG. 21 is a side view of the spring element according to FIG. 19.

FIG. 19 shows a perspective view of a spring element 60 according to another sample embodiment for a jaw 11 according to FIG. 4, FIG. 20 shows a side view of the said spring element 60, and FIG. 21 a side view of this spring element 60. Here an evenly rounded spring surface 91 is provided, on which in the middle here four ribs 61 are provided, the activation of which by application of pressure corresponds to the activation in the direction of the arrows 73, 83 or 98.

FIG. 22 shows a partially sectional side view of a screw 16, a nut 21 and a safety screw 109 for a clamping element 10 according to one of the figures. The cone 23 of the nut 21 can be smooth, but it can also exhibit exterior threading. Then the bore 15 should preferably be at least partially provided with a threading. The casing 23 of the nut 21 has a through bore with a first narrow segment 111 that exhibits interior threading for the acceptance of the outer threading of the screw 16. A wider segment 112 connecting to it has a shoulder 113, on which the screw head of the safety screw 109 can rest. The safety screw 109 is provided to be screwed into an interior threading 114 in the point of screw 16. In particular, it can also be provided, for example by means of an adhesive or other means, that after a pre-assembly of a clamping element 10, the screw 16 cannot be detached from the threading 114, so that the unity of the clamping element is assured.

Figure 23:
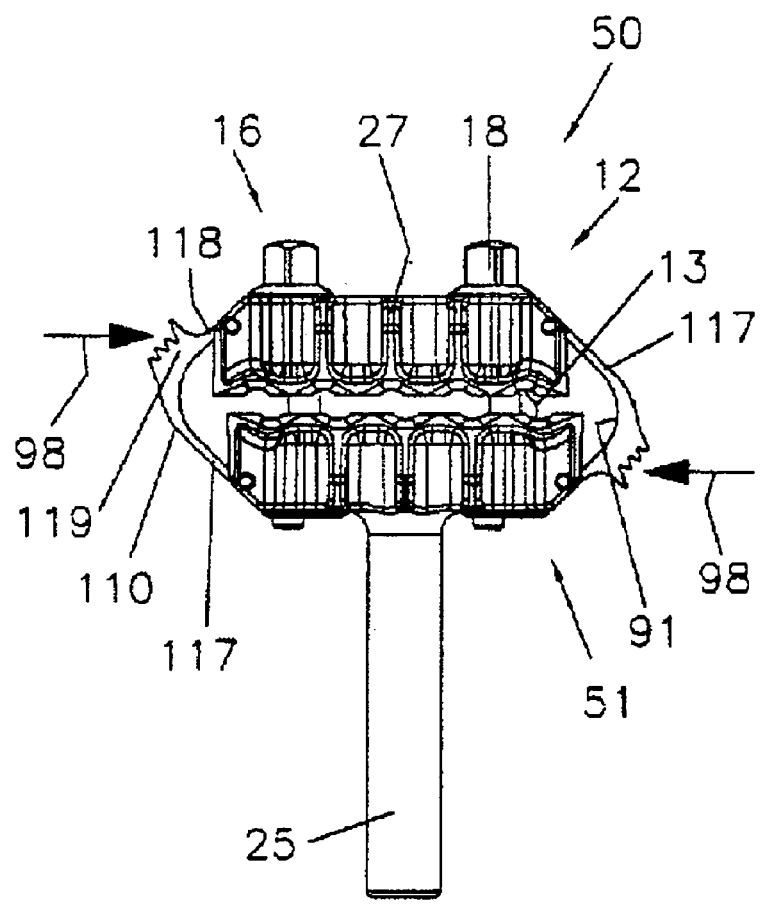
FIG. 23 is a side view of a fifth sample embodiment of a clamping element according to the invention, without pins.
Figure 24:
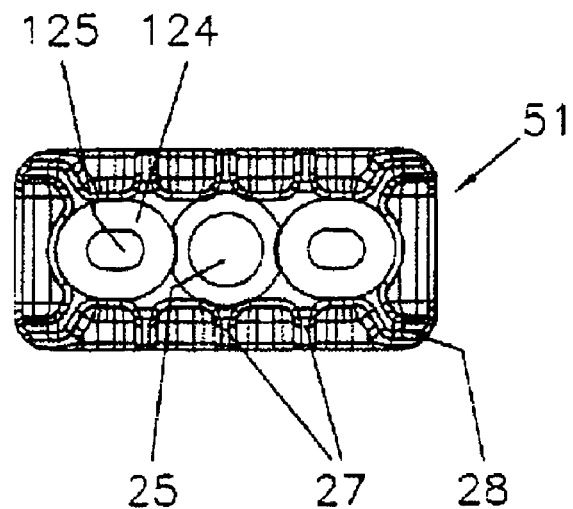
FIG. 24 is a top view of the clamping element according to FIG. 23.

FIG. 23 shows a side view of a fifth embodiment of the clamping element 50 pursuant to the invention, without pins. FIG. 24 shows a top view of the clamping element 50 according to FIG. 23. The one jaw 12 corresponds for example to the corresponding jaw 12 from FIG. 1. Opposite it is arranged another jaw 51, to which here, for example, a rod 25 is affixed. It may also be without rods or be designed according to FIG. 15. The jaws 12 and 51 have the previously-described small round through holes 95 for the acceptance of a spring element 110. This spring element 110 is preferably asymmetrically-shaped and has a longer leg 117 and a shorter leg 118, which pass through an activating component 119 and into each other. The spring element 110 is shaped like the spring element 90 according to FIG. 1, i.e. it is tightened in the position shown in FIG. 23 and holds the two jaws 12 and 51 opposite each other. By means of pressure corresponding to the arrows 98 perpendicular to the main axis of the jaws 12 and 51 these may swing toward each other. Thus the position of one jaw 12 against the other jaw 51 forms an angled or swinging motion, whereby the grooves 13 not originally lying opposite each other are swung into place opposite each other and thereby the two front surfaces of the jaws 12 and 51 are separated from each other in order to push in the pins 100.

In this case the ends of the screws 16 reach all the way through the jaws 51 in the manner shown in FIG. 24. For this reason, in the jaw 51 there are two oblong through holes 125 provided, which are surrounded by a conical or stepped indentation or casing mounting 124, in order to accept the nut 21. In this case a solution with a self-tapping screw or threading in the hole 125 is not practical.

At a resting position the inserted but not tightened screws 16 should preferably be in the area of the one end of each oblong hole 125, for example in FIG. 24 on the right side of the drawing. In exerting pressure to open the jaws 12 and 51 in the direction of the arrow 98, the screws 16 move in their casings 23 on the left side of the drawing in FIG. 24 and at the same time the casings 23 of the nuts 21 go deeper into their mountings 124 or the screw heads 18 into their mountings 24.

FIG. 25 shows a schematic side view of a sixth embodiment of a clamping element pursuant to the invention, without pins, and FIG. 26 shows a schematic side view of a seventh sample embodiment of a clamping element 140 pursuant to the invention, without pins. The construction of the jaws 71 can be designed similar to the jaws 41 according to FIG. 9 and 10 (with or without rod, etc.). What is important is the provision of springs 70 around the screws 16 to push the jaws 71 together. In the embodiment shown here, the screws each end in a threaded bore or casing in the jaw that lies opposite. In principle, the spring 70 next to a screw 16 that reaches through may also be fixed to the opposite side and may be supported between jaw 71 and nut 21, which is not shown in the figure.

The spring element 120 in the embodiments shown in FIGS. 25 and 26 is a leaf spring 120. In FIG. 25 each one is provided at its ends with a through bore, in order, with the help of 121, to fix it onto the opposite ends of jaws 117. By pressure in the direction of the opposing arrow 98, the leaf springs 120 are opened and thus the space between the jaws 71 opens wider against the elastic force of the springs 70.

In the embodiment of FIG. 26, the ends 123 of the leaf springs 120 (shown in FIG. 25) are each pushed into the slots 122 shown schematically, in which they may be held by adhesive or by means of the existing tension. The ends may be flat or may include points on the side or middle.

Preferably the material of the spring elements 90, 80, 60 should be softer material than that of the jaws 11, 12, 31, 32, 41, 51, 71. The spring elements 90, 80, 60 are plugged and are held in the mountings 85 or 95 by means of their inherent spring force. They may also be clamped or glued into these mountings or 2K-injected. The same is true for the spring element 120, which may be a metallic or non-metallic leaf spring.

The spring elements 90, 80, 60, 120 are provided with a leaf spring in the center. On the free ends of the leaf spring 91, which are to be inserted into bearings 85, 95, 122, corresponding bearing knobs 82, 92 are provided, that extend away from stem 83, 93. In this way the spring element 90, 80, 60, 120 is held between the spring mounting ribs 28. In other embodiments not shown here, these knobs may be inserted from the outside into a single center or into two adjacent center spring-mounted ribs. It is important, however, that the leaf spring 91 cover an area that can be held and pressed together by the user of the clamping element, in order to move the jaws apart. It must be determined that the spring elements 90, 80, 60, 120 do not experience any force that is exerted by the pins 100 on the jaws 11, 12, 31, 32, 41, 51 and 71, when the screws 16 are tightened. This applies also for any force exerted on the rod 25.

It is also possible for both jaws 11, 12, 31, 32, 41, 51, 71 together with the spring elements 90, 80, 60, 120 to be fabricated by injection molding by means of co-injection, also known as 2K-injection technique, so that a one-piece clamping element results. In addition, it is also possible to design such a one-piece clamping element 90, 80, 60, 120 with springs 70, whereby then the spring elements 90, 80, 60, 120 may be designed without elastic function.

From the drawings it may be seen that some jaws 11, 31, and 41, have a correspondingly-shaped rod 25 that is guided parallel to the locking screws 16 into the base. It may also take another direction in a further course. Other jaws 12, 32, 51, 71 have such a rod 25 and have at its base a bore 115, as described in connection with FIG. 15. This bore 115 may be so designed that a corresponding rod 101 may be inserted and locked.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A clamp for bone pins comprising:
   a first jaw member having a bone pin engaging surface including a plurality of elements for locating a plurality of bone pins;
   a second jaw member having a bone pin engaging surface, the first and second jaw members each having first and second ends;
   a pair of clamping elements extending through said first and second jaw members for moving said bone pin engaging surfaces towards another; and
   a pair of spring elements each engaging an external surface at the first and second ends of said first and second jaw members spaced from said pin engaging surfaces acting to bias the bone pin contacting surfaces of said first and second jaw member towards one another while allowing respective first and second ends of the first and second jaw members to move apart to accommodate the plurality of bone pins,
   wherein each of the pair of spring elements engage external surfaces of said first and second jaw members,
   wherein the spring elements are in the form of a C-shaped leaf spring that exhibits connecting knobs on its free ends that is received within recesses in each of said jaw members, and that the leaf spring exhibits at its center a direct flat manipulation area or an activation area that is realized through ribs,
   wherein a force acting from the outside onto the manipulation area or activation area of both spring elements reduces the curvature of each of the spring elements which results in a relative movement between said first jaw member and said second jaw member apart from each other such that said bone pins can be introduced.

2. The clamp as set forth in claim 1 wherein said clamping elements are threaded elements extending through bores in both said first and second jaw members.

3. The clamp as set forth in claim 1 wherein said plurality of bone pin locating elements are grooves formed in the pin engaging surfaces of said first and second jaw members.

4. The clamp as set forth in claim 1 wherein said recesses are formed on external surfaces extending generally perpendicular to said pin engaging surfaces.

5. A clamp for clamping bone pins comprising:
   a first and second opposing jaw member each having at least two corresponding bone pin locating grooves for the acceptance of a corresponding number of bone pins, each groove having a bone pin engaging surface,
   wherein two arc-shaped spring elements are provided, with which in the resting position, the jaws are tensed towards a closed position and further comprising means for locking the jaws in the closed position,
   each spring element acting on opposite first and second ends of each first and second jaw member while allowing the respective first and second ends of each jaw member to move apart to accommodate the two bone pins wherein the jaws have spaces on their lateral ends, from which small rod-shaped elements protrude, into which ends or connecting elements of the spring elements may be retained, wherein the spring elements are in the form of a C-shaped leaf spring that exhibits connecting knobs on its free ends that is received within recesses in each of said jaw members, and that the leaf spring exhibits at its center, an arched activation area that is realized through ribs, wherein a force acting on a convex side of the activation area of both spring elements reduces the curvature of each of the spring elements which results in a relative movement between said first jaw member and said second jaw member away from each other.

6. The clamp as set forth in claim 5, wherein the means for locking includes at least one through bore provided in each of the jaws, which bores are vertical to the level of the adjoining jaw and are aligned to one another and suitable for the acceptance of a locking element.

7. The clamp as set forth in claim 6, wherein the locking element consists of a screw that may be inserted into the bore of one jaw and a complementary interior-threaded nut that can be inserted into the other jaw, so that the clamp can be locked by turning the screw in the nut.

8. The clamp as set forth in claim 5, wherein the spring elements and the jaws consist of plastic, whereby the plastic of the spring elements is softer or more flexible than the plastic of the jaws.

9. The clamping element as set forth in claim 5, wherein the bone pin locating grooves are set parallel to each other.

10. A clamp for bone pins comprising: a first jaw member having a bone pin engaging surface including a plurality of elements for locating a plurality of bone pins;
a second jaw member having a bone pin engaging surface, the first and second jaw members each having first and second ends;
a pair of clamping elements extending through said first and second jaw members for moving said bone pin engaging surfaces towards another; and
first and second arc-shaped spring elements acting to bias the bone pin contacting surfaces of said first and second jaw member towards one another, the first arc-shaped spring element mounted on an external surface of the first end of the first and second jaw members, the second arc shaped spring element mounting on an external surface of the second end of the first and second jaw member; each arc-shaped spring element having a concave side facing the end surfaces of the first and second jaw members, wherein each spring elements are in the form of a C-shaped leaf spring that exhibits connecting knobs on its free ends, and that the leaf spring exhibits at its center a direct flat manipulation area or an activation area that is realized through ribs, said knobs received within recesses in each of said jaw members,
whereby a force acting on said flat manipulation area or said activation area of a convex side of the arc-shaped spring element reduces the curvature of each of the spring elements which moves the first and second jaw members apart.

11. The clamp as set forth in claim 10, further comprising a locking element consisting of a screw that may be inserted into a bore of one of said first and second jaw element and a complementary interior-threaded nut that can be inserted into the other of said first and second jaw element, so that the clamp can be locked by turning the screw in the nut.

12. The clamp as set forth in claim 10, wherein the jaws have spaces on their lateral ends, from which small rod-shaped elements protrude, into which ends or connecting elements of the spring elements may be retained.

13. The clamp as set forth in claim 10, wherein the spring elements and the jaws consist of plastic, whereby the plastic of the spring elements is softer or more flexible than the plastic of the jaws.

14. The clamping element as set forth in claim 10, wherein the first and second jaw members have bone pin locating grooves that are set parallel to each other.

\* \* \* \* \*

UNITED STATES PATENT AND TRADEMARK OFFICE
CERTIFICATE OF CORRECTION

PATENT NO.       : 7,618,417 B2                                    Page 1 of 1
APPLICATION NO.  : 11/108492
DATED            : November 17, 2009
INVENTOR(S)      : Thomke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1021 days.

Signed and Sealed this

Twenty-sixth Day of October, 2010

David J. Kappos
*Director of the United States Patent and Trademark Office*